US005674493A

United States Patent [19]

Strayer

[11] Patent Number: 5,674,493
[45] Date of Patent: Oct. 7, 1997

[54] COMPOSITIONS AND METHODS FOR TARGETING CELLS WITH A2R AND A2R MONOCLONAL ANTIBODIES

[75] Inventor: David S. Strayer, Newtown Square, Pa.

[73] Assignee: Thomas Jefferson University, Philadelphia, Pa.

[21] Appl. No.: 176,218

[22] Filed: Dec. 30, 1993

Related U.S. Application Data

[63] Continuation-in-part of Ser. No. 114,951, Aug. 31, 1993.
[51] Int. Cl.$^6$ ............................................. A61K 39/395
[52] U.S. Cl. ............................. 424/152.1; 424/183.1; 530/388.2; 530/391.7; 435/7.21
[58] Field of Search .................... 530/388.2, 391.7; 435/240.27, 172.2, 70.21, 7.21; 424/152.1, 183.1

[56] References Cited

U.S. PATENT DOCUMENTS 5,045,451 9/1991 Uhr et al. .

OTHER PUBLICATIONS

Waldman, Science 252:1657–1662.
Harris et al. Tibtech 11:42–44, 1993.
Buchsbaum et al., Med Phys. 20:551–567, 1993.
Harlow et al. "Antibodies a Laboratory Manual", Cold Spring Harbor Press, 1988 pp. 324–326 and 591–592.
Houghton et al. Seminars in Oncology 13:165–179 1986.
D.S. Strayer (1991), "Identification of a Cell Membrane Protein That Binds Alveolar Surfactant", Am. J. Pathol.138, 1085–1095.
D.S. Strayer (1992), "Applications of Anti–Curosurf Antibodies to Understanding the Biology of Alveolar Surfactant", Biol. Neonat., 61, 1–14.
D.S. Strayer, Hallman, M. and Merritt, T.A. (1991) "Immunogenicity of surfactant. II. Porcine and bovine surfactants ", Clin. Exp. Immuno.,83, 41–46.
Weinstein et al., "Regional Delivery of Monoclonal Antitumot Antibodies: Detection and Possible Treatment of Lymph Node Metastases", Cancer Metastasis: Experimental and Clinical Strategies (Alan R. Liss, Inc.), pp. 169–180 (1986).

Primary Examiner—Toni R. Schneiner
Attorney, Agent, or Firm—Law Offices of Jane Massey Licata

[57] ABSTRACT

Compositions for delivering imaging and therapeutic agents through use of the monoclonal antibodies A2C and A2R or fragments thereof are provided. Methods for delivering selected effector molecules such as imaging, modulating and therapeutic agents through use of these compositions are also provided.

3 Claims, No Drawings

COMPOSITIONS AND METHODS FOR TARGETING CELLS WITH A2R AND A2R MONOCLONAL ANTIBODIES

This application is a continuation-in-part of application Ser. No. 08/114,951, filed Aug. 31, 1993.

INTRODUCTION

This invention was made in the course of research funded by the U.S.P.H.S. (Food and Drug Administration) under grant number FD-R-000461. The U.S. government may have certain rights in this invention.

BACKGROUND OF THE INVENTION

Therapeutic agents can be delivered by a multitude of routes, methods, formulations and techniques. The primary object in selecting a delivery system for a therapeutic agent is to maximize the positive effects of the agent while minimizing the unwanted side effects.

Monoclonal antibodies have been proposed as a possible means of detecting and treating tumors (Weinstein et al., Cancer Metastasis: Experimental and Clinical Strategies (Alan R. Liss, Inc.), pp. 169–80 (1986)). Monoclonal antibodies specific for identified antigens on the membranes of tumor cells have been used in attempts to direct imaging agents and therapeutics, which often have very detrimental side effects, to the cancerous cells. An advantage of monoclonal antibodies over classical diagnostic agents and treatments is that with monoclonal antibodies it should be possible to specifically target selected cells. Clinical studies with monoclonal antibodies, however, have frequently been unsatisfactory. One of the reasons for this is the difficulty in identifying an antigen found only on a specific target or tissue. Monoclonal antibodies, like all other drugs and therapeutic agents, have little value unless they can be targeted to a specific target or tissue.

A physiologically active substance, called "pulmonary surfactant" exists in the lungs. Pulmonary surfactant is mainly biosynthesized in and secreted from type II epithelial cells of the alveoli and is known to be present as an internal lining of the wall of the whole respiratory tract including the alveolar region. It is known that pulmonary surfactant reduces the surface tension of the alveoli and prevents collapse of the alveoli. In addition, pulmonary surfactant plays an important role as a defense mechanism in the entire respiratory tract. It is well documented that it prevents pulmonary edema and has preventative effects on bacterial or viral infection and on atmospheric pollutants and antigens which induce inflammation of the respiratory tract or asthmatic attacks. Pulmonary surfactant is also known to play an important role in lubricating the respiratory lumen and expelling foreign matter from the respiratory tract by activating mucociliary transport.

Pulmonary surfactant is a complex mixture of proteins and phospholipids. There are four known proteins in alveolar surfactant; SP-A, -B, -C, and -D. SP-B and -C are small, very hydrophobic proteins that interact with phospholipids to lower alveolar surface tension. SP-D is a 43 kDa apoprotein of uncertain function. Like SP-A, SP-D has collagen-like domains. SP-A is a moderately hydrophobic 29–36 kDa apoprotein. It reportedly stabilizes the phospholipid structure and promotes interactions between phospholipids. It also appears to be important in regulating surfactant secretion. These proteins, together with phospholipids, are secreted from alveolar type II pneumocytes and form the air-liquid interphase in the alveoli and comprise what is referred to herein as "alveolar surfactant".

The development of two monoclonal antibodies directed against the antigen binding regions of antibodies to surfactant proteins have recently been reported (D. S. Strayer (1991) Am. J. Pathol. 138, 1085–1095 and D. S. Strayer (1992) Biol. Neonat., 61, 1–14). These independently derived anti-idiotype antibodies, A2C and A2R, bind anti-SP-A antibodies and prevent them from binding surfactant protein. These antibodies have been described in terms of their functional characteristics and have been structurally characterized in copending patent application Ser. No. 08/114,951. In addition to being useful in identifying cell membrane molecules on type II cells that are important in regulating alveolar surfactant secretion, it has now been found that these antibodies may be used as targeting agents for assisting in the delivery of therapeutic agents to type II cells or bronchial epithelial cells.

SUMMARY OF THE INVENTION

Compositions and methods are provided for targeting type II cells or bronchial epithelial cells that also bear the SPAR antigen. In preferred embodiments, the monoclonal antibodies A2C and A2R are employed in combination with a therapeutic agent to target these therapeutic agents to type II or bronchial epithelial cells. Such compositions may be useful in delivery of cytotoxic, sensitizing, radioactive or imaging agents to these cells, in genes therapy of these cells or in directing stimulatory or inhibitory substances to these cells.

DETAILED DESCRIPTION OF THE INVENTION

As used herein, "alveolar surfactant protein" refers to the apoproteins associated with alveolar surfactant described herein below. The human lung is composed of a large number of small sacs or alveoli in which gases are exchanged between the blood and the air spaces of the lung. The exchange is mediated by the presence of alveolar surfactant which is a complex substance that lines the epithelial surface of the lung. The surfactant is composed of phospholipid components and protein components. The surfactant-associated protein comprises both serum protein and surfactant-specific apoproteins. There are three major surfactant-specific proteins. One is a water-soluble protein having a molecular weight of 29–35 kDa (alveolar surfactant protein SP-A) and the other two are very hydrophobic proteins having molecular weights of 9 kDa (SP-B) and 3.5 kDa (SP-C). Granular pneumocytes (type II alveolar cells) secrete the surfactant material.

"Alveolar surfactant protein SP-A" refers to the relatively high molecular weight (29–35 kDa) apoprotein associated with the pulmonary surfactant. The nucleic acid sequence of SP-A is known.

Anti-idiotype antibodies were used to identify a non-Ig cell membrane protein that binds SP-A. Use of anti-idiotype antibodies is predicated on the premise that if two molecules (in this case anti-SP-A antibody and SP-A receptor) bind the same ligand (SP-A), their ligand binding sites may be similar. A variety of cell membrane receptors have been characterized using this approach. Thus, to identify SP-A receptor, a group of monoclonal antibodies (Mabs) that bind surfactant protein were used. Many of these Mabs both bind SP-A and inhibit its function. This population undoubtedly possesses a diverse range of idiotypic regions. One or more of their SP-A binding regions could mimic the SP-A receptor ligand binding site.

Two rats immunized independently with different combinations of monoclonal anti-SP-A antibodies produced anti-idiotype antisera that recognized SP-A-binding sites of different anti-SP-A Mabs. From these animals, two monoclonal anti-idiotype antibodies were produced. Each of these bound anti-surfactant antibody and prevented surfactant binding by anti-surfactant antibody. The antibodies, A2R and A2C, also both recognize the same approximate 30 kDa non-Ig protein on rabbit, pig, and human alveolar cell membranes and inhibit surfactant binding by these cells. Simultaneously, an approximately 31 kDa pulmonary protein binds recombinant SP-A. A2R and A2C bind a protein on the cell membrane of alveolar and bronchial cells but not macrophages, lymphocytes, and other cells. When cellular surfactant binding capacity is saturated by preincubating cells or tissue sections with surfactant, A2C and A2R no longer bind these cells. Thus, A2C and A2R MaAbs and surfactant protein all bind the same cell membrane structure.

A2C and A2R also weakly bind higher molecular weight species present in Y1089 cells infected with recombinant, but not wild type, λgt11. The larger species may be a multimer or aggregate of SPAR protein or may alternatively represent aberrant transcripts or a larger SPAR protein in which a translational stop signal has been ignored.

The distribution of SPAR transcripts is consistent with their origin in type II alveolar cells. Immunohistochemical analysis and in situ hybridization studies indicate that SPAR is expressed in prominent and protruding alveolar cells, usually located at corners of alveoli. The same location is seen in the alveolar cells that express SP-B and SP-C and is consistent with and characteristic of type II alveolar pneumocytes. Cells that make SPAR transcripts and proteins are not consistent in appearance or location with type I pneumocytes, alveolar macrophages, interstitial cells, or stromal cells. These observations indicate that SPAR is made by type II pneumocytes. Unlike SP-B and SP-C, SPAR is also expressed in ciliated airway lining cells but not, apparently, in Clara cells, suggesting that SPAR (or a like protein) may have functions in several cell types.

Therefore, SPAR proteins are SP-A recognition structures on alveolar cells. They may represent the whole SP-A receptor or only an SP-A binding portion thereof.

The effect of an antibody to SP-A binding protein on type II cell membranes on surfactant secretion was tested. Results indicated that the A2C and A2R monoclonal antibodies specifically interfered with SP-A mediated inhibition of surfactant secretion. Knowledge of these antibodies and their specificity for type II cells and bronchial epithelial cells containing the SP-A receptor, is useful in targeting therapeutic agents to the lung. In the present invention, the term "therapeutic agent" refers to any molecule or group of molecules expected to have an effect upon or produce some change in the targeted cells. The potential agents which can be conjugated to at least one chain of the A2C or A2R antibody targeted to type II cells are considerable. Only a few will be recounted here.

In one embodiment, the therapeutic agent comprises a chemotherapeutic agent. For example, an individual afflicted with a tumor of bronchial or type II cell origin may be amenable to therapy in which either the A2C or A2R antibody is complexed to or used to direct through a vehicle such as liposomes a cytoxic or radioactive agent to the tumor cells. In another embodiment, these antibodies are conjugated to a sensitizing agent which, when combined with another therapeutic modality, could improve the specificity of a cytotoxic therapy for tumors of type II or bronchial epithelial cells.

These antibodies could also be used in imaging. Clinical pulmonologists or neonatologists often have a need to determine functional type II cell mass and/or distribution. In this embodiment, at least one chain of one or both of the antibodies are attached to a radiologically active substance and used to localize the radiologically active substance to type II cells. Examples of radiologically active substance include, but are not limited to, radionucleides used for conventional imaging such as $^{99m}Tc$ and radionucleides used in magnetic resonance imaging such as $^{13}C$. The localized radioactivity can then be quantitated or visualized by techniques well known to diagnostic radiologists or nuclear medicine physicians.

The antibodies are also useful in the direction of stimulatory or inhibitory substances such as tumor necrosis factor, PGE, TGFB, IL-6, terbutaline cyclic nucleotides, to type II or bronchial epithelial cells. In this embodiment, a stimulator or inhibitor which are referred to herein as a "modulating agent", may be specifically targeted to a selected cellular target. For example, a cytokine that stimulates surfactant production, but is toxic to many cells at the required therapeutic concentration, is incorporated into a delivery vehicle such as a liposome which has one or both antibodies attached. This vehicle-antibody combination permits delivery of a high concentration of the toxic cytokine to the specific cellular target. Thus, agents intended to inhibit or stimulate the target cell function can be delivered specifically to these target cells without the adverse complications and unwanted side effects often associated with such agents.

These antibodies could also be used in genes therapy of type II cells. In some diseases such as congenital alveolar proteinosis, it has been established that afflicted individuals are deficient in a surfactant protein. This deficiency appears to reflect a genetic defect in the genes in question. Gene replacement targeted at type II cells could correct this deficiency. One method for carrying out this gene therapy is to clone the surfactant protein B gene or its cDNA from either the gene's own promoter or from another promoter. This construct is then incorporated into liposomes or engineered vectors which are targeted to type II cells through one or both of the A2C or A2R antibodies. The liposome or vector containing the construct can then be administered so that the construct can be incorporated into the targeted cells with the intent of rectifying the deficiency.

These antibodies could also be applied to gene therapy by redressing transient but life-threatening deficiencies in surfactant or other type II cell product. A liposome, targeted using A2C and/or A2R, could be used to insert a surfactant protein gene controlled by a powerful promoter into type II cells in order to induce the synthesis of large amounts of surfactant.

A2R and A2C could also be used to target stimulatory or inhibitory agents to the bronchial epithelium that bears SPAR-like protein on its cell membrane. Thus, for example, if an agent is found that can modulate bronchial mucous secretion, A2R and/or A2C could be used to target such an agent to the bronchial epithelium to decrease or increase mucous secretion. Such an agent might be used, for example, to decrease mucous secretion in chronic bronchitis or asthma.

Antibodies and antibody fragments of A2C and A2R are encompassed by the instant invention. "Antibody fragments" which contain the idiotype of the molecule can be generated by well known techniques. For example, such fragments include but are not limited to the $F(ab')_2$ fragment which can be produced by pepsin digestion of the antibody molecule; the Fab' fragments which can be generated by reducing the disulfide bridges of the $F(ab')_2$ fragment; and the F(ab) fragments which can be generated by treating the antibody with papain.

It is also contemplated that humanized antibodies can be produced and utilized in the present invention. Nonhuman antibodies can induce an immune response in humans. Recombinant DNA techniques minimize this problem by "humanizing" nonhuman monoclonal antibody (MAb) genes. The productively rearranged IgG genes of the hybridoma can be identified by Southern blot analysis by comparison of the patterns of hybridizable bands obtained from restricted DNA of the hybridoma and its parent myeloma using V region probes for the light and heavy chain genes. Size-fractionated DNA containing the productively rearranged genes can be cloned into lambda phage and identified by screening with V region probes. Subsequently, the variable region of the cloned genes can be subcloned into a plasmid containing the human constant region genes. Further humanizing of the nonhuman-human chimeric antibody genes may be achieved by oligonucleotide site-directed mutagenesis. Oligonucleotides containing the sequence coding for human framework regions with flanking nonhuman sequences can be annealed to the nonhuman-human antibody plasmids, transfected into $E.\ coli$, and mutated plasmids identified by hybridization with oligonucleotides. By this approach, nonhuman framework sequences would be converted to human sequences so that only the complementarity determining regions (CDRs) will contain the nonhuman sequence. Plasmids containing the humanized genes can be expressed by the transfection of light and heavy chain genes into a nonhuman non-producing myeloma cell line, for example.

As used herein, the term "antibody" is meant to refer to complete, intact antibodies, Fab fragments, and $F(ab)_2$ fragments and includes chimeric and humanized antibodies. It is preferred that antibodies be complete, intact antibodies. The protein structure of complete intact antibodies, Fab fragments and $F(ab)_2$ fragments and the organization of the genetic sequences that encode such molecules are well known.

As used herein, the term "chimeric antibody" is meant to refer to antibodies which consist of a constant region from an antibody derived from a first species and a variable region in which either the entire variable region or at least a portion of the variable region is derived from a second species.

As used herein, the term "hybrid variable region" refers to a variable region that comprises portions derived from at least two different species. Generally, a hybrid variable region consists of framework sequences from one species and CDRs from a different species.

As used herein, the term "humanized antibodies" is meant to refer to chimeric antibodies that comprise constant regions from human antibodies and hybrid variable regions in which most or all of the framework sequences are from a human variable region and all or most of the CDRs are from a non-human variable region. Chimeric antibodies are produced by well known recombinant techniques and readily available starting materials. Such techniques are described, for example, in UK Patent Application GB 2,188,638 A.

Compositions comprising one or both of the A2C and A2R antibodies or fragments thereof in combination with a selected effector can be administered at selected concentrations to bind to the type II cells or bronchial epithelial cells. Various delivery systems can be used for therapeutic delivery of these compositions. Methods of introduction include but are not limited to intradermal, intramuscular, intraperitoneal, intravenous, subcutaneous, and intranasal routes. Also intratracheal or intrabronchial administration as aerosol is contemplated. These compositions can also be encapsulated in liposomes. Various pharmacological vehicles can be utilized in order to deliver these compositions. Any suitable pharmaceutical agent with desirable solubility characteristics and chemical properties may be used, including but not limited to, where appropriate, saline or dextrose. These compositions may also be combined with a vehicle. "Vehicle", as used herein, means a substance, usually without therapeutic action, used as a medium for the administration of a therapeutic or modulating agent.

Compositions comprising at least one chain of an A2C or A2R monoclonal antibody or a fragment thereof and a selected effector are provided. The selected effector comprises a therapeutic agent, an imaging agent or a modulating agent. In one embodiment, a composition comprising the antibody and a therapeutic agent, such as a cytotoxin or a gene replacement construct, is prepared, either alone or in combination with a sensitizing agent. In another embodiment, the antibody is combined with a selected imaging agent such as $^{99m}Tc$ or $^{13}C$. In yet another embodiment, the antibody and a selected modulating agent, such as a cytokine, are administered either alone or in combination with a selected vehicle.

Methods of delivering the selected effectors to cells whose surfaces bear the SPAR antigen are also provided. In these embodiments, at least one chain of an A2C or A2R monoclonal antibody or a fragment thereof is complexed with the selected effector. The antibody-effector complex is then contacted with the targeted cells having SPAR antigens on their surfaces. In this way, the selected effectors are effectively delivered to the cells.

SP-A Binding Activity in Lung Homogenates—A2C and A2R anti-idiotype monoclonal antibodies both bind a 30 kDa alveolar cell membrane protein in three different animal species. Proteins from rabbit lung (and heart, as a negative control) were electrophoresed using SDS-PAGE, blotted to PVDF and treated with $^{125}I$-labeled purified recombinant human SP-A to ascertain if a lung protein of similar size also binds SP-A. It was found that a lung protein of approximately 30 kDa binds SP-A. Thus, normal lung proteins of approximately 30 kDa bind SP-A and A2C and A2R anti-idiotype antibodies.

Binding of SP-A by Cloned Proteins—Proteins encoded by cDNA clones were analyzed for their ability to bind SP-A. In lysogenic phage colonies, IPTG was used to induce expression of the cloned protein. Proteins were prepared from these lysogeny, and their ability to bind SP-A was tested. Results were obtained for the 4.1 kb human cDNA. Identical results were obtained using its porcine counterpart. An approximately 31 kDa protein encoded by the cDNAs and expressed in λgt11 binds radiolabeled SP-A. *Escherichia coli* infected with wild type λgt11 show no such SP-A binding activity.

Simultaneously, it was ascertained that the anti-idiotype MaAbs principally recognize proteins of similar size in these preparations. A2R and A2C also slightly bind higher molecular weight species in these, but not control, preparations. Preparation expressing the approximate 31 kDa protein from the porcine 1.8 kb cDNA reacted similarly.

SPAR mRNA: Tissue Distribution and Distribution within the Lungs—RNA was prepared from organs of New Zealand White rabbits and BALB/c mice, slot-blotted to nitrocellulose, and probed with $^{32}P$-labeled 1.8 kb cDNA. Rabbits and mice make mRNA that hybridizes with pSPAR cDNA. This mRNA was expressed by in situ hybridization.

Biotinylated 1.8 kb SPAR cDNA was used to detect SPAR transcripts in formalin-fixed tissues from normal mice. SPAR mRNA was seen in cells consistent in appearance and location with type II pneumocytes. It was also found in ciliated cells of the conducting airways. Type I alveolar, pulmonary interstitial, and stromal cells were all negative. The alveolar cellular distribution of SPAR transcripts is similar to that of SP-B and SP-C. Other tissues tested (liver, spleen, heart, kidney) did not express detectable SPAR. These results regarding SPAR mRNA detection are consistent with immunohistochemical experiments in which A2C and A2R were used to detect SPAR protein in tissue sections.

Effect of Antibody on Alveolar Surfactant Secretion—Pulmonary surfactant secretion from lung epithelial type II cells can be stimulated with a wide variety of agents including isoproterenol and ATP. Purified SP-A inhibits the secretion of lung surfactant in vitro. The effect of an antibody to an SP-A binding protein on type II cell membranes on surfactant secretion was tested. The results are shown in Table I.

TABLE I

|  | % Lung Surfactant Secretion in 2 hours | |
| --- | --- | --- |
|  | − Antibody | + Antibody |
| Experiment 1: 50 ng/ml SP-A, 20 µg/ml antibody | | |
| ATP | 1.7 | 2.5 |
| ATP + SP-A, 50 ng/ml | 0.7 | 1.6 |
| Experiment 2: 50 ng/ml SP-A, 50 µg/ml antibody | | |
| ATP | 5.9 | 9.0 |
| ATP + SP-A, 50 ng/ml | 4.3 | 6.3 |
| Experiment 3: 100 ng/ml SP-A 20 and 50 µg/ml antibody | | |
| ATP | 2.9 | 3.5 (20 µg/ml) |
|  |  | 3.1 (50 µg/ml) |
| ATP + SP-A, 100 ng/ml | 0.9 | 2.0 (20 µg/ml) |
|  |  | 2.4 (50 µg/ml) |

For each experiment shown in Table I, the top line indicates surfactant secretion without SP-A and the bottom line with SP-A, showing that SP-A inhibits secretion. The first column is without the antibody and the second column with the antibody. The data shows that the antibody promotes secretion (blocks the inhibition). Each experiment was conducted with a separate cell preparation. Experiments for each condition were conducted in duplicate and averaged to provide mean values. Each observation was within 10% of the mean value. These results indicated that this antibody may be a suitable agent to counteract in inhibition of secretion by SP-A.

The invention is further illustrated by the following, non-limiting examples.

EXAMPLES

Example 1

Proteins—Purified, recombinant human surfactant protein A was the kind gift of Dr. Mikko Hallman (Univ. of California, Irvine). *Staphylococcus aureus* protein A was purchased from Calbiochem. Procedures for radioiodination using chloramine T (Sigma) are well known in the art. For example see, D. S. Strayer, Hallman, M. and Merritt, T. A. (1991) *Clin. Exp. Immuno.*, 83, 41–46.

Monoclonal Antibodies—The production and characterization of A2C and A2R monoclonal anti-idiotype antibodies have been described (D. S. Strayer (1991) *Am. J. Pathol.* 138, 1085–1095 and D. S. Strayer (1992) *Biol. Neonat.*, 61, 1–14). F344 rats were immunized with mixtures of rat monoclonal antibodies (MaAb) directed against porcine and rabbit surfactant proteins. Anti-idiotype antisera were assayed by inhibition of surfactant binding to anti-surfactant MaAb. Two different rats, each immunized against different combination of anti-surfactant MaAbs, produced detectable titers of anti-idiotype antibodies. Spleen cells from these rats were fused. Each fusion yielded one monoclonal anti-idiotype antibody that inhibited binding of surfactant protein to the respective anti-surfactant antibodies. A2C and A2R are thus independently derived anti-idiotype monoclonal antibodies, directed against other antibodies.

Tissues for Analysis—Organ tissues from normal female New Zealand White rabbits and normal female BALB/c mice (Jackson Laboratories) were removed aseptically and snap-frozen in liquid nitrogen. Tissues were homogenized (Polytron, Brinkmann Instruments) and RNA prepared (RNAzol, Cinna BioTex). Proteins from these tissues were solubilized and prepared for electrophoresis by boiling in 0.1% SDS, 50 mM 2-mercaptoethanol (Sigma).

Example 2

Protocol for Pulmonary Surfactant Secretion Studies—For studies on pulmonary surfactant secretion, alveolar epithelial type II cells were isolated from lungs of specific pathogen free male Sprague-Dawley rats (180–200 grams body weight) according to well known methods. In brief, lungs were digested with elastase (3 units/ml), and the free cells were plated on IgG coated bacteriological tissue culture plates for 1 hour. The unattached cells were collected by "panning" and contained approximately 65% type II cells. These cells were suspended in minimum essential medium (MEM) containing 10% fetal bovine serum and plated on tissue culture plastic dishes. At this stage, 0.3 µCi of [$^3$H-methyl] choline was added to the medium, and the cells incubated at 37° C. and in humidified air containing 5% $CO_2$ for the next 20–22 hours. During this period, type II cells attach to the plastic and the cellular lipids are labeled with radioactive choline. Using this protocol greater than 95% of the radioactivity in the phosphatidylcholine (PC) of lipid fraction is routinely recovered. At the end of the incubation period, the cells attached to tissue culture plates were washed five times, and fresh medium MEM without fetal bovine serum (1.5 ml) plated on the cells. To some of the plates, the antibody A2R was added at the indicated concentration. After incubation for 15 minutes, the indicated amount of SP-A (purified from rat lung surfactant) was added to some plates and all plates were incubated for another 15 minutes. At the end of 30 minutes of incubation, medium from 2 plates was removed, and analyzed for release of surfactant lipids during this 30 minute period (zero time). To other plates, 1 mM ATP or MEM (control) was added and incubation continued for the next 2 hours. At the end of this incubation, medium from each plate was removed, and both the cells and the medium for each condition were extracted for lipids after addition of egg PC as a carrier lipid and [$^{14}$C]-dipalmitoyl glycerophosphocholine as a tracer lipid to improve and correct for recoveries of surfactant lipids. The radioactivity in the lipid fractions was measured and corrected for recovery during lipid extraction which exceeded 90%. The surfactant secretion was then expressed as percent of total cellular phosphatidylcholine. (% Surfactant Secretion=radioactivity in the medium lipids× 100/radioactivity in the lipids of medium plus cells.) Results (Table III) are presented as secretion during 2 hours incubation and after subtraction of secretion during the first 30 minutes incubation.

Example 3

A2C and/or A2R may be used to target type II cells or bronchial epithelial cells that bear the SPAR antigen to deliver cytotoxic agents to these cells. The antibodies are either complexed to or are used to direct (e.g., via liposomes) a selected cytotoxic agent or radioactive agent and administered to an individual with a tumor of bronchial or type II cell origin. The antibodies may also be conjugated to a sensitizing agent which, when combined with another therapeutic modality, improves the specificity of the cytotoxic therapy for tumors of type II or bronchial epithelial cells. Methods of conjugating antibodies are well known in the art and selecting appropriate amounts and combinations of agents is well within the skill of the artisan. The "cytotoxic agent" may also include a gene or DNA fragment that could be used to control or direct cellular proliferation and/or gene expression.

Example 4

For diseases such as congenital alveolar proteinosis, in which it has been established that afflicted individuals are deficient in a surfactant protein, A2C and/or A2R may be used in gene therapy of type II cells. The surfactant protein B or its cDNA are cloned in accordance with well known methods, either downstream from its own promoter or from another promoter. The construct is targeted to type II cells using liposomes or an engineered vector in which one or both of the antibodies is used to target the cells.

Example 5

For use in imaging, A2C and/or A2R is attached to a radiologically active substance such as $^{99m}$Tc for conventional imaging or $^{13}$C for MRI. The antibody is used to localize the radiologically active substance to type II cells. This localization is then quantitated or visualized in accordance with well known techniques by diagnostic radiologists or nuclear medicine physicians. In this way, it is possible to determine type II cell mass and/or distribution.

Example 6

A2C and/or A2R may be used to direct a modulating substance (stimulatory or inhibitory substance) such as TNF or PGE, to type II or bronchial epithelial cells. For example, a cytokine that stimulates surfactant production but is toxic to many cells at the needed concentrations is packaged in a vehicle which is attached to one or both antibodies. The vehicle-antibody combination allows delivery of the cytokine without adverse effects on other cells. Method of preparing compositions of modulating agents and vehicles are well known in the art.

What is claimed:

1. A composition for delivering a therapeutic agent to cells whose surfaces bear the SPAR antigen comprising an A2C or A2R monoclonal antibody or a fragment thereof and a therapeutic agent.

2. The composition of claim 1 wherein the therapeutic agent comprises a cytotoxin.

3. A method for delivering a therapeutic agent to cells whose surfaces bear the SPAR antigen comprising complexing at least one chain of an A2C or A2R monoclonal antibody or fragment thereof with a therapeutic agent and contacting the antibody-agent complex with the targeted cells having SPAR antigene on their surface, thereby delivering the therapeutic agent to cells whose surfaces bear the SPAR antigen.

* * * * *

UNITED STATES PATENT AND TRADEMARK OFFICE
CERTIFICATE OF CORRECTION

PATENT NO. : 5,674,493

DATED : Oct. 7, 1997

INVENTOR(S) : Strayer

It is certified that error appears in the above-indentified patent and that said Letters Patent is hereby corrected as shown below:

In the title: after "WITH" please delete "A2R" and insert therefor --A2C--

At col 1, line 3, after "WITH", please delete "A2R" and insert therefor --A2C--.

At col 10, line 35, please delete "antigene" and insert therefor --antigens--.

Signed and Sealed this

Tenth Day of February, 1998

Attest:

BRUCE LEHMAN

Attesting Officer

Commissioner of Patents and Trademarks